United States Patent [19]

Cortes et al.

[11] Patent Number: 4,629,705
[45] Date of Patent: Dec. 16, 1986

[54] INDIRECT-PHOTOMETRIC CHROMATOGRAPHY DONE IN AND WITH A VARIABLE CAPACITY WEAKLY BASIC OR ACIDIC ION EXCHANGE COLUMN

[75] Inventors: Hernan J. Cortes; Timothy S. Stevens, both of Midland, Mich.

[73] Assignee: The Dow Chemical Company, Midland, Mich.

[21] Appl. No.: 615,985

[22] Filed: May 31, 1984

[51] Int. Cl.$^4$ ............... G01N 31/08; G01N 21/00
[52] U.S. Cl. ......................... 436/161; 73/61.1 C; 210/656
[58] Field of Search ............. 73/61.1 C; 210/635, 210/656, 659; 422/70; 436/161

[56] References Cited

U.S. PATENT DOCUMENTS

| | | | |
|---|---|---|---|
| 3,920,397 | 11/1975 | Small et al. | 436/100 X |
| 3,923,460 | 12/1975 | Parrott et al. | 73/61.1 C X |
| 3,925,019 | 12/1975 | Small et al. | 73/61.1 C X |
| 4,086,222 | 4/1978 | Lindquist et al. | 210/635 X |
| 4,101,460 | 7/1978 | Small et al. | 210/198.2 X |
| 4,133,753 | 1/1979 | Takeuchi et al. | 210/656 X |
| 4,290,892 | 9/1981 | Abbott | 210/656 |
| 4,383,047 | 5/1983 | Stevens et al. | 521/28 |
| 4,414,842 | 11/1983 | Small et al. | 73/61.1 C |
| 4,486,311 | 12/1984 | Nakajima et al. | 210/635 |

FOREIGN PATENT DOCUMENTS

| | | | |
|---|---|---|---|
| 2914807 | 10/1980 | Fed. Rep. of Germany | 210/659 |
| 53-60291 | 5/1978 | Japan | 436/161 |
| 58-72054 | 4/1983 | Japan | 436/161 |

OTHER PUBLICATIONS

Helfferich; Ion Exchange; 1962 Ed; McGraw-Hill Book Co.; New York, N.Y.
Khym; Analytical Ion-Exchange Procedures in Chemistry and Biology, Theory, Equipment, Techniques; 1974 Ed. Prentice-Hall, Englewood Cliffs, New Jersey.
Small et al; Novel Ion Exchange Chromatographic Method Using Conductimetric Detection; Anal. Chem., vol. 47, No. 11, Sep. 1975, pp. 1801-1809.
Snyder et al; Introduction to Modern Liquid Chromatography; 1979 Ed.; John Wiley & Sons; New York, N.Y.
Molnar et al; High-Performance Liquid Chromatography of Ions; J. Chrom. 201 (1980) pp. 225-240.
Stevens et al; Hollow Fiber Ion-Exchange Suppressor for Ion Chromatography; Anal. Chem. 53 (1981) pp. 1488-1492.
Skelly; Separation of Inorganic and Organic Anions on Reverse-Phase Liquid Chromatography Columns; Anal. Chem. 54 (1982) pp. 712-715.
Cortes; High-Performance Liquid Chromatography of Inorganic and Organic Anions Using Ultraviolet Detection and an Amino Column; J. Chrom. 234 (1982) pp. 517-520.
Small et al; Indirect Photometric Chromatography; Anal. Chem. 54 (1982) pp. 462-469.
Haddad et al; High-Performance Liquid Chromatography of Inorganic and Organic Ions Using Low-Capacity Ion-Exchange Columns with Indirect Refractive Index Detection; J. Chrom. 252 (1982) pp. 177-184.
De Ligny et al; Influence of Salt Composition, Ionic Strength, and pH on the Distribution Coefficient of Ribonuclease in Gel Permeation Chrom. J. Chrom. Sci. 21(4) 1983, pp. 174-178.

Primary Examiner—Barry S. Richman
Assistant Examiner—Michael S. Gzybowski

[57] ABSTRACT

A versatile and highly sensitive procedure of indirect photometric chromatography in which a variable capacity pH dependent weakly basic or weakly acidic ion exchange medium is used in the chromatographic column to effect ion separations. Adjusting eluent pH allows increased detection limits without extended analysis time, reduced column efficiency, or the need for a battery of conventional strongly basic/acidic ion exchange columns.

13 Claims, 10 Drawing Figures

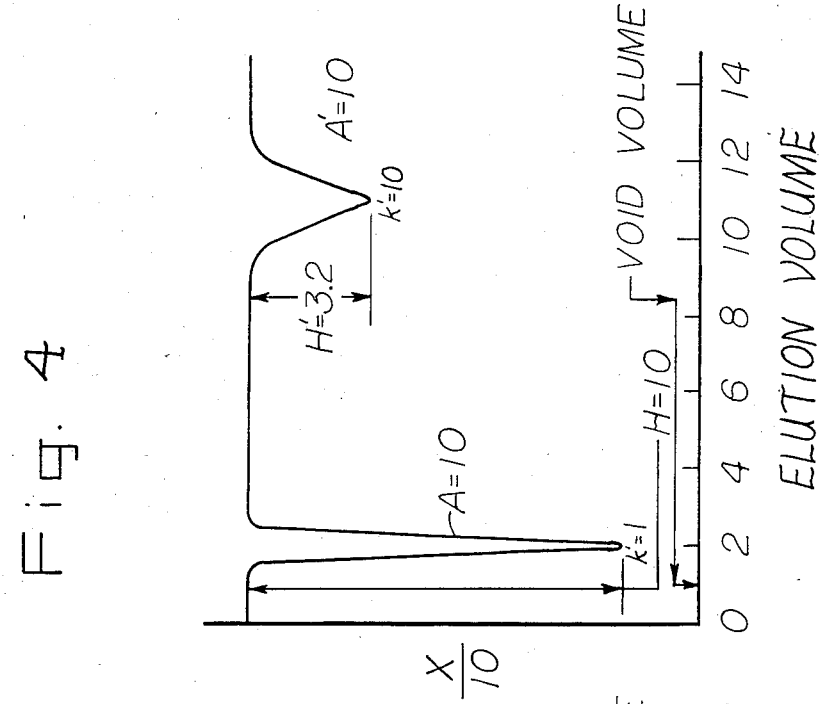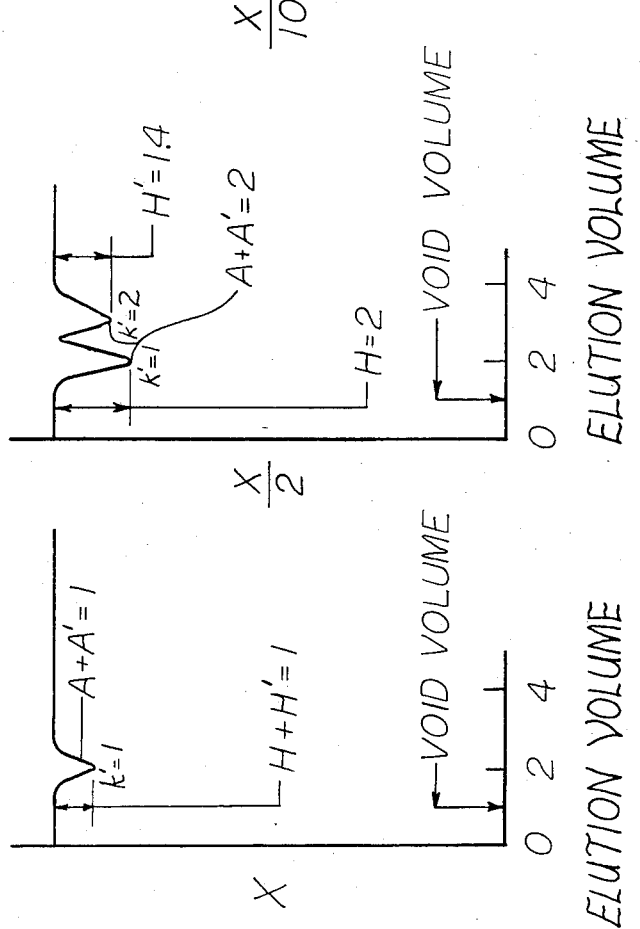

Eluent - 0.01 M PHTHALIC ACID
Flow - 2.0 ml/min.
pH. - 2.56
DETECTOR - UV @ 302 nm
SAMPLE - 1000 µg/ml Cl⁻
A.U.F.S. - 0.2
INJECTION - 50 µl Eluent - 0.001 M PHTHALIC ACID
pH. - 3.7
DETECTOR - UV @ 295 nm
SAMPLE - 1000 µg/ml Cl⁻
A.U.F.S. - 0.2
INJECTION - 50 µl @ 2.0 ml/min.

Eluent - 0.001 M PHTHALIC ACID
pH. - 3.7
DETECTOR - UV @ 295 nm
SAMPLE - 1000 µg/ml Cl⁻
A.U.F.S. - 0.2
INJECTION - 50 µl @ 2.0 ml/min.

"ZORBAX-NH₂"
0.02M Phthalic Acid
pH 2.9

1 — 33 ppm F⁻
2 — 100 ppm I⁻
3 — 50 ppm NO₃⁻
4 — 40 ppm Cl⁻
5 — 340 ppm PO₄³⁻
6 — 500 ppm SO₄²⁻

"IBM-NH₂"
0.002M Phthalic Acid
pH 3.6

1 — 10 ppm I⁻
2 — 4 ppm Cl⁻
3 — 5 ppm NO₃⁻
4 — 34 ppm PO₄³⁻
5 — 50 ppm SO₄²⁻

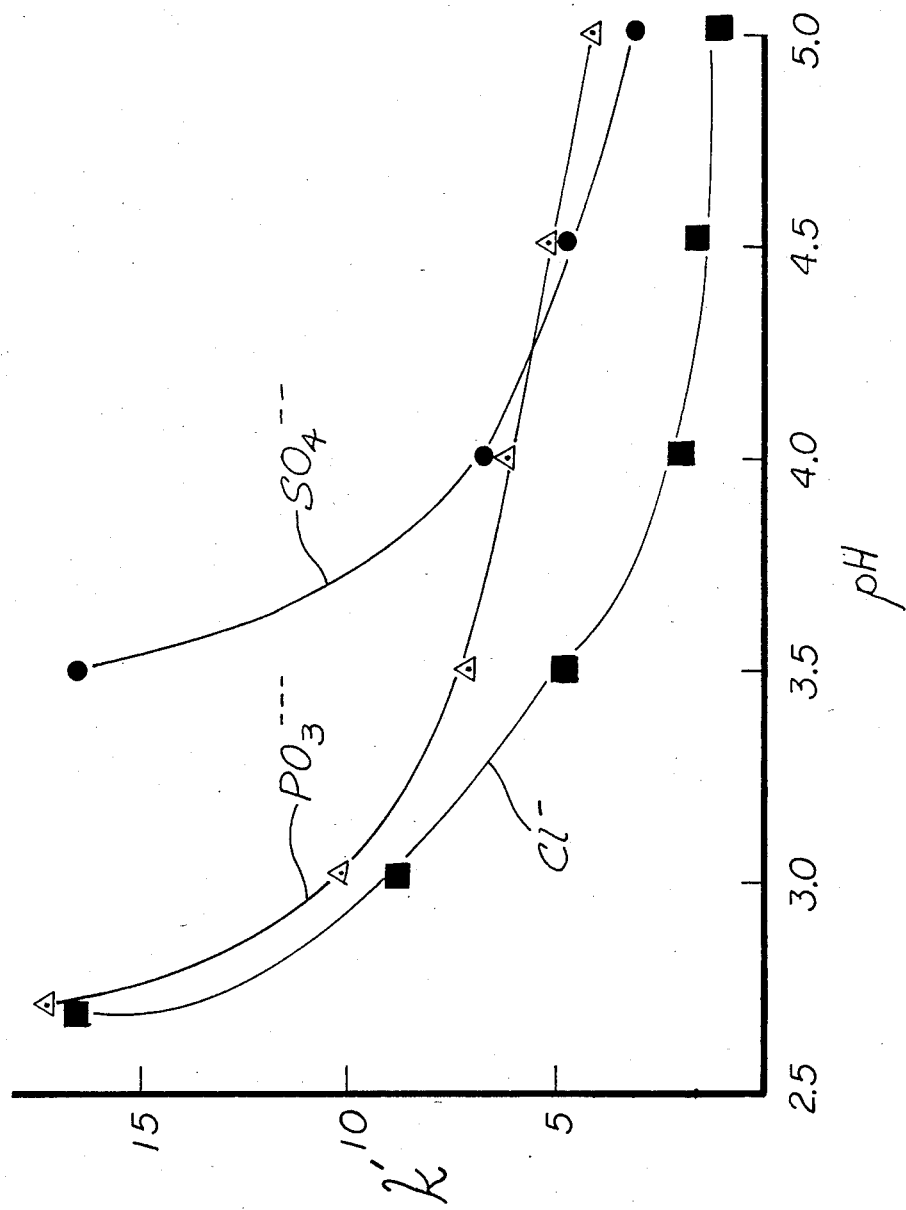

INDIRECT-PHOTOMETRIC CHROMATOGRAPHY DONE IN AND WITH A VARIABLE CAPACITY WEAKLY BASIC OR ACIDIC ION EXCHANGE COLUMN

BACKGROUND OF THE INVENTION

High Pressure Liquid Chromatography (i.e., "HPLC") has in the past been extensively developed and applied in the field of ion analysis. Technical literature relating to prior HPLC methods for ion analysis relevant to this invention is identified below:

| Reference Number | Source Identification |
| --- | --- |
| (I) | "ANALYTICAL ION-EXCHANGE PROCEDURES IN CHEMISTRY AND BIOLOGY, Theory, Equipment, Techniques" By Joseph X. khym, 1974 Ed., Published by PRENTICE-HALL, INC. of Englewood Cliffs, New Jersey 07632; |
| (II) | N. E. Skelly, Anal. Chem., 54 (1982) 712; |
| (III) | I. Molnar, H. H. Nauer and D. Wilk, J. Chromatogr., 201 (1980) 225; |
| (IV) | H. J. Cortes, J. Chromatogr., 234 (1982)517; |
| (V) | H. Small, T. S. Stevens and W. C. Bauman, Anal. Chem., 47 (1975) 1801; |
| (VI) | H. Small and T. E. Miller, Anal. Chem., 54 (1982) 462; |
| (VII) | United States Letters Patent No. (i.e., "U.S."): 3,920,397; |
| (VIII) | T. S. Stevens, J. C Davis, and H. Small, Anal. Chem., 53 (1981) 1488; |
| (IX) | United States Letters Patent 4,383,047;; |
| (X) | United States Letters Patent 4,414,842; |
| (XI) | P. R. Haddad and A. L. Heckenberg, J. Chromatogr., 252 (1982) 177; |
| (XII) | "ION EXCHANGE" by F. Helfferich, 1962 Ed., Published by McGraw-Hill Book Company, Inc. of New York City (New York) 10017; and |
| (XIII) | "INTRODUCTION TO MODERN LIQUID CHROMATOGRAPHY" by L. Snyder and R. Kirkland, 1979 Ed., Published by John Wiley & Sons, New York City (New York) 10017. |

As is brought forth in Ref. (II), HPLC analysis of inorganic and organic ions which absorb in the ultraviolet region has been accomplished on reverse phase liquid chromatographic columns having pendant functional ion-exchange groups. Ref. (IV) is illustrative of a similar analysis when relying on direct ultraviolet light (i.e., "UV") detection after separation on an amino column. Those anions and cations which do not absorb in the UV region can be determined by conductimetric detection, as is evidenced, e.g., by Refs. (V) and (VIII). Ion analysis is also possible by the use of the more recent liquid chromatographic procedure known as Indirect Photometric Chromatography (i.e., "IPC").

Small and Miller reported IPC in Ref. (VI) and in patent Ref. (X). As brought out in their original work, sensitive detection of the analyte ions is obtained using dilute eluents according to the expression:

$$\frac{\text{Signal (from Detector)}}{\text{Noise}} \propto \frac{C_s}{N \cdot C_e} \quad \text{(I)}$$

wherein:

$C_s$ is the concentration of the sample ion being analyzed;

N is the random noise which is generated or occurs in the system; and $C_e$ is the monitor/displacing ion concentration of the eluent ion.

However, the use of diluent eluents to obtain high sensitivity in IPC can lead to high k' values when used together with conventional strong base and strong acid ion-exchange chromatography columns. These strong base (and acid) ion-exchange columns can be modified, e.g., by physically shortening the column to reduce k', but this also produces a detrimental reduction in the theoretical plate count of the shortened column. The invention is concerned with overcoming this disadvantage of IPC procedures.

TERMS

"Photometric Monitoring" as used in the following Summary of the Invention means monitoring using as the detector, a UV-vis spectrophotometer (the most advantageous form of the invention); a fluorescence spectrophotometer; an infrared (IR) spectrophotometer; or a refractive index (RI) detector.

"Monitor/Displacing" ions means eluent ions which can be detected using photometric monitoring. Most advantageously, the monitor/displacing ions comprise UV-absorbing ions.

"Transparent Ions" means and refers to sample ions which are generally non-responsive to photometric monitoring whereby the presence of the sample ions in the effluent is generally not observed by the detector. However, perfect transparency is not required, and the term "transparent" in its broad interpretation is meant to include sample ions having less of the monitored property than the monitor/displacing ions, and which can be indirectly quantitated by photometrically monitoring decreases in the concentration of the monitor/displacing ions.

"Weakly Basic (and Acidic) Ion Exchange Medium" means and includes any weakly basic (and acidic) ion exchanger or ion exchange medium, the capacity of which is pH dependent without highly significant efficiency loss over a range of pH values. Included within this term are reverse phase columns converted to be used in an ion exchange mode.

"Overloading" means the condition where the ratio of available ion-exchange capacity of the column or medium, expressed for example in equivalents per column, to the total number of equivalents of sample ions in the injected sample is 10 or less.

"Maximum Potential Ion-Exchange Capacity" means for a given ion-exchange column or medium, the ion-exchange capacity in equivalents per column or equivalents per gram at a pH two units less than B in equation II, following, for a weak base ion-exchanger; and a pH two units greater than B in equation II, following, for a weak acid ion-exchanger.

SUMMARY OF THE INVENTION

The invention is a method for the chromatographic analysis of transparent sample ions in a solution of photometrically monitorable liquid effluent wherein generally:

sample is contacted with a flow-through ion exchange medium, and an elution through said ion exchange medium is performed using a liquid eluent which contains photometrically detectable monitor/-displacing ions that effectually displace sample ions off the involved ion exchange medium so as to eventually cause displaced sample ions to appear in the effluent from the ion exchange medium;

there is utilized an eluent containing said monitor/displacing ions which are photometrically detectable in said effluent and which are of the same charge but not necessarily the same valence as the sample ions to be detected;

said effluent is photometrically monitored and the concentration of transparent sample ions of interest eluting from the ion exchange medium is indirectly quantitated based on the fluctuation(s) caused by same in the effluent response as produced by the appearance of the transparent sample ions in the effluent causing a concurrent and proportional dip in the concentration of the observed monitor/displacing ions in the effluent;

using a pH dependent variable capacity ion exchange medium that is weakly basic in nature when anions are to be detected and determined from said sample making contact with said medium and using a weakly acidic ion exchange medium when cations are so involved; and using an eluent, the pH of which controls the capacity of the ion exchange without detrimentally affecting efficiency to a capacity within the range encompassed on the lower end, by the condition which produces overloading, and on the upper end, by a capacity which is not greater than about 50 percent of the maximum potential ion exchange capacity of the ion exchange medium.

In preferred forms of the invention, several interrelated variables are controlled to produce what is termed a "balance factor" of between about 1 to about −3, and most preferably about 0 to about −2. Specifically, balance factor is a numerically expressed relationship between the pH of the eluent, the concentration of the eluent monitor/displacing ions, and the characteristics of the specific weakly basic or weakly acidic column used for the analysis, calculated as follows:

$$\text{Balance Factor} = \sqrt{(A - B)^2} - \left(\log \frac{1}{C}\right)$$

wherein:
$A$ = the pH of the eluent;
$B$ = the inflection point, in terms of A, of the curve of $k'$ of an ion of interest in an analysis versus A for a fixed eluent displacing ion concentration used for the analysis;
$C$ = the molar concentration of the eluent displacing ion used for the analysis.

In practicing the invention, it is advantageous to use dilute eluents for purposes of obtaining sensitive detection. Generally, eluents will be used containing $5 \times 10^{-3}$ molar or less of monitor/displacing ions. Lower concentrations can be used advantageously in the method, e.g., typically concentrations of $5 \times 10^{-4}$ molar and less monitor/displacing ions are used in order to achieve low detection limits.

A beneficial aspect of the invention is that it permits the practitioner to adjust the capacity of the employed mass of the ion exchange medium simply by fixing the pH of the eluent; and make concurrent downward adjustments in eluent monitor/displacing ion concentration in order to improve sensitivity. This adjustment involves neither a physical modification of the column or a detrimental loss of column efficiency.

THE DRAWING

Yet further objectives, aspects and advantages of the invention will, in part, be pointed out and, in part, apparent from the following detailed description considered together with the accompanying Drawing wherein:

FIGS. 2–4 are idealized chromatograms which graphically illustrate differences between strongly basic (and acidic) ion exchangers and the variable capacity ion exchangers of the present invention;

FIG. 8 is a plot illustrating the dependency of column capacity (in terms of $k'$) on the eluent pH.

DETAILED DESCRIPTION

Figure 1:
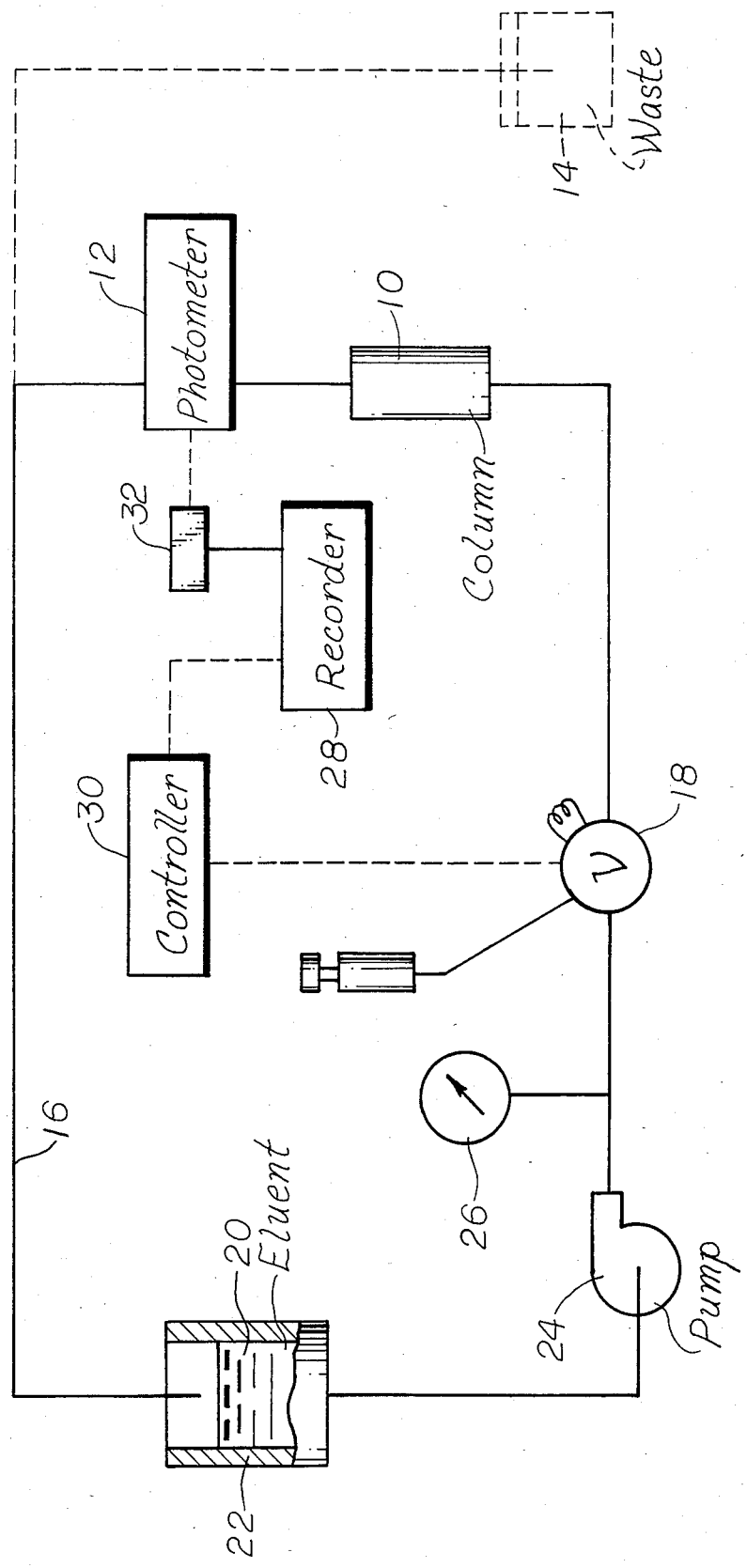
FIG. 1 is an elevational view of apparatus for performing ion exchange chromatography with indirect photometric detection in accordance with the principles and teachings of the present invention.

Referring to FIG. 1, there is shown a typical schematic of an ion exchange chromatography apparatus which is desirably used in practicing the invention. The apparatus comprises a chromatographic column 10 which is packed with a weakly basic (or acidic) ion exchange medium. Column 10 is followed by a photometric detector 12, preferably a variable wavelength UV-vis spectrophotometer with flow through cell design for HPLC applications. The effluent of the detector is dispelled to waste vessel 14 or to recycle, e.g., through a line 16.

Sample is preferbly added, e.g., by syringe injection to the system at a sample injection valve 18 which may be automatically operated by a controller 30. The injected sample is swept through the apparatus by a solution containing photometrically detectable monitor/displacing ions, i.e., eluent solution 20 drawn from an eluent reservoir 22 by a chromatographic pump 24. The eluent pressure is monitored by a pressure gauge 26, and is passed through the sample injection valve 18 to column 10. The solution (effluent) leaving column 10 with the ionic species resolved suitably for detection is conveyed by a liquid conduit to detector 12.

In the photometric detector, the presence of the monitor/displacing ions in the effluent produces an electrical signal which is proportional to the amount of such ions. The detector signal is displayed, e.g., by a strip chart recorder 28 optionally equipped with and electronic device 32 to provide additional base line biasing voltage. A chromatogram is thus developed showing decrements or peaks, e.g., depending on the polarity of the signal outputted by the detector. These decrements (or peaks) are caused by and proportional to transparent sample ion bands passing through the detector. Thus, the transparent sample ions may be indirectly quantitated as a function of the observed decreases in the monitor/displacing ions as each transparent or partly transparent sample ion band passes through the detector.

SUITABLE WEAKLY BASIC (AND ACIDIC) ION EXCHANGE MEDIUMS

The invention uses weakly basic or weakly acidic ion exchangers which are typically ceramic (e.g., silica) or polymeric based materials. The effective capacity of these ion exchangers is controlled and determined by appropriate adjustments to the pH of the eluent. By so determining and fixing the column capacity, a nondetrimental dilution of the eluent monitor/displacing ion concentration can occur to attain enhanced detection sensitivity (as measured by peak height). This can occur without greatly increasing, while maintaining, or even while decreasing k', and without compromising column efficiency. Broadly the columns are operated according to the invention between the condition which produces column overloading on the low capacity end; and at the high capacity end, a capacity which is not greater than about 50 percent of the maximum ion exchange capacity of the column. More commonly, and for optimum advantage, the columns are operated at between about 0.1 to 30 percent of their maximum ion exchange capacity.

Suitable weak base ion exchangers which are utilizable in practice of the present invention are (without limitation thereto), tertiary, secondary or primary amines of the representative structure:

$$R-\underset{\underset{H}{|}}{\overset{\overset{H}{|}}{N}} 1°, R-\underset{\underset{R}{|}}{\overset{\overset{H}{|}}{N}} 2°, R-\underset{\underset{R}{|}}{\overset{\overset{R}{|}}{N}} 3° \quad (III)$$

These are adequately disclosed in Ref. (I) and other of the identified Refs. and are well known to those skilled in the art.

The capacity of the weakly basic or weakly acidic ion-exchange medium contemplated herein is regulated and can be changed and adjusted by alteration of its environmental pH. Thus, an inactive weak base can be represented by the structures above. With an appropriate and calculated pH alteration, an active ion-exchanging weak base structure is representable as:

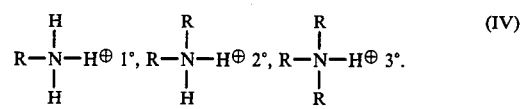

The capacity of ion exchangers of this structure is typically expressed in microequivalents per gram (i.e., "$\mu$eq/g"). For illustrative (non-limiting) purposes, the following correlatives are given to show capacity dependence of a weakly basic ion exchanger as a function of pH: 20 $\mu$eq/g @ pH 1; 18 @ 2; 2 @ 3; 0.2 @ 4; 0.1 @ 6; and nil or substantially nil @ 7. The broadly-operable pH range is between 0 and about 8 for a silica based (silicious) ion exchanger medium (which tends to degrade at pH $\geq$ 8). A pH in the range of about 2 to about 6 is usually preferable to maximize column life of a silica based ion exchange medium.

Cation determinations using the improved IPC technique of the present invention are done with a column having a weakly acidic ion exchange medium or packing; the most common and easily available representatives of which have negatively charged carboxylate (i.e., "—COO−") functional ion exchange structure. With such weakly acidic silica based chromatographic materials, the broadly operable range of effectuated pH is from about 1 up to 8—preferably between about 2 and about 7. The maximum capacity(ies) of weakly acidic ion exchangers of this type occur when operating in the higher or more basic range of pH values with lower capacities produced by adjusting the eluent pH downwardly to more acidic values. The "Chromegabond WCX" column available commercially from ES Industries in an example of a weakly acidic column which may be beneficially used in the practice of the present invention.

COMPARATIVE ILLUSTRATION

A graphical comparison between a single fixed capacity strong acid or base ion-exchanger of the prior art and a variable capacity weak acid or base packing in a single column is presented in the form of the idealized chromatogram resembling views of FIGS. 2-4. In these representations, the concentration of the monitor/displacing ions is plotted along the ordinate as a normal or given concentration {x} in FIG. 2; a half-strength $$\frac{\{x\}}{2}$$

concentration in FIG. 3; and a tenth-strength $$\frac{\{x\}}{10}$$

concentration in FIG. 4. The area A' designated in each of FIGS. 2, 3 and 4 is that expected using a strongly basic or strongly acidic ion exchange column. The symbol H' is indicative of the peak (or dip) height developed as a result of the same prior art. For comparative purposes the analogous peak areas and heights attained through the practice of the invention are identified in these Figures by the symbols A and H.

In FIG. 2, A and A', H and H' are identical. In FIG. 3, the eluent is diluted two-fold with the illustrated effect, namely a two-fold increase in A and A'. However, H is greater than H' and thus H is more detectable than H'. Also, the peak resulting from the prior art is wider and elutes later than the peak resulting from the practice of the present invention.

In FIG. 4, the eluent of FIG. 1 is diluted ten-fold with the illustrated effect, namely a ten-fold increase in A and A'. However, H is much greater than H' and thus is much more detectable. Also, the peak A' resulting from the prior art is undesirably much wider and elutes much later than the peak A resulting from the present invention.

In these implementations of the invention, the capacity of the single column weak base or acid ion exchanger is reduced by pH adjustment in step with eluent dilutions, thereby maintaining k'=1. In contrast with the invention, the single column strong base or acid ion exchanger shows progressively increasing and worsening k' values in inverse relationship to eluent dilutions, eventually resulting in a lengthy analysis time (k'=10, FIG. 4).

The invention is yet further illustrated and its features and advantages disclosed by reference to the following teaching Examples.

EXAMPLE 1

The dependence of retention time of various anions vs. phthalic acid eluent concentration and eluent pH was studied on a weak base ion exchange system and is reported in this Example. It is shown that a decrease in eluent concentration in these systems leads to an increase in sensitivity without loss of theoretical plate count, allowing sensitivity requirements to be met by simple adjusting eluent conditions.

The liquid chromatograph apparatus of this study comprised an Altex Model 110 A pump; a Rheodyne Model 7125 injection valve equipped with a 50 µl loop; a LC55 (Perkin-Elmer) variable wavelength UV detector and a Sargent Model SRG recorder.

The weakly basic ion exchange medium used was a 250×4.6 mm I.D. Zorbax® NH2 column (available from duPont Instruments, Wilmington, Del., U.S.A.). This column was converted to the ion-exchange mode by washing the column with ~100 ml each of acetonitrile, methanol, water, then eluent in that order. Initial equilibration of the column required up to 200 ml of eluent flow.

The eluent consisted of phthalic acid in water, adjusted to various pH values with NaOH. Flow rate was 2.0 ml/min. Detection was by UV at 290-310 nm. Column pressure was 1500 psig and operating temperature was 24° C.

Figure 5A:
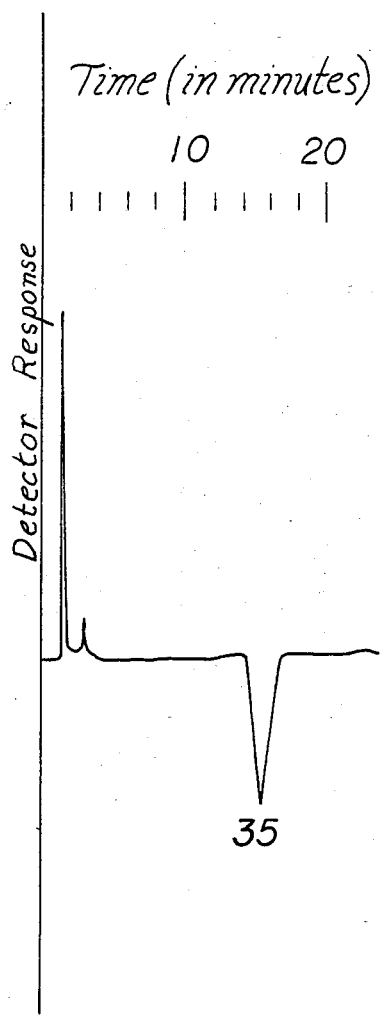
FIGS. 5a–5c are reproduced chromatograms developed using the method of the invention, and are associated with the teaching of Example 1.
Figure 5B:
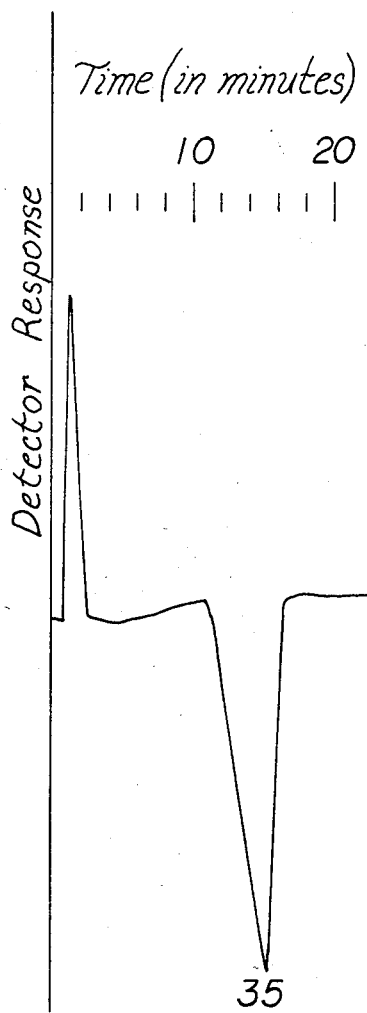
Figure 5C:
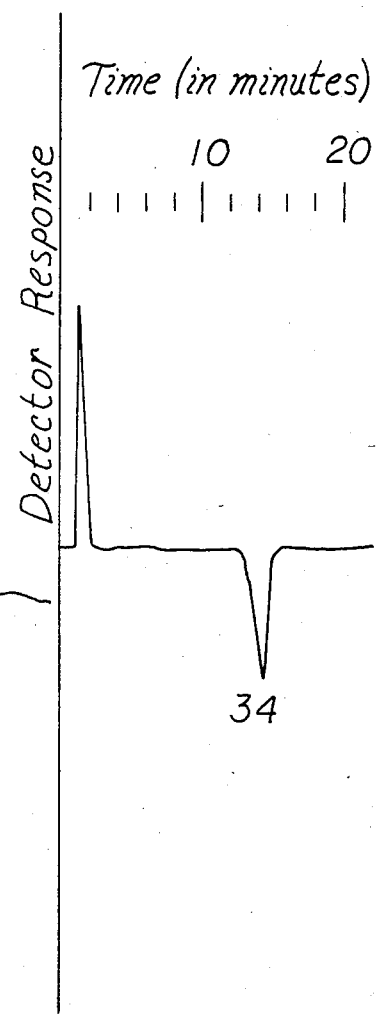

The results of using the described system at varying pH and eluent concentrations is shown in the reproduced chromatograms of FIGS. 5a–5c using as the sample ion, injections of Cl⁻ ion. In the chromatograph of FIG. 5a, the eluent concentration is a factor of 10 times greater than in FIGS. 5b and 5c. The chloride ion peak area in FIG. 5b as expected is thus about ten times larger than that in FIG. 5a; however, the "Peak Height" in FIG. 5b is not ten times larger than that in FIG. 5a. This is due to column overloading by the 1000 µg/ml of chloride sample ion. The overload arises due to the reduced column capacity resulting from the use of a higher eluent pH. The chloride ion peak in FIG. 5c does not show the effect of overloading when the concentration of chloride ion injected was reduced to 100 µg/ml. A comparison of FIGS. 5a and 5c indicates that the use of a ten-fold reduction in eluent strength with an amino column results in a ten-fold increase in sensitivity without an increase in analysis time and without excessively reduced theoretical plate count.

Additionally, the study shows that the theoretical plate count for the peak in FIG. 5c is about the same as that in FIG. 5a. This would not have occurred if a conventional strong base ion exchange column had been reduced in length. If such a column gave 800 theoretical plates for a 25 cm length, 80 theoretical plates would be the expected plate count for a 2.5 cm long column.

Figure 6:
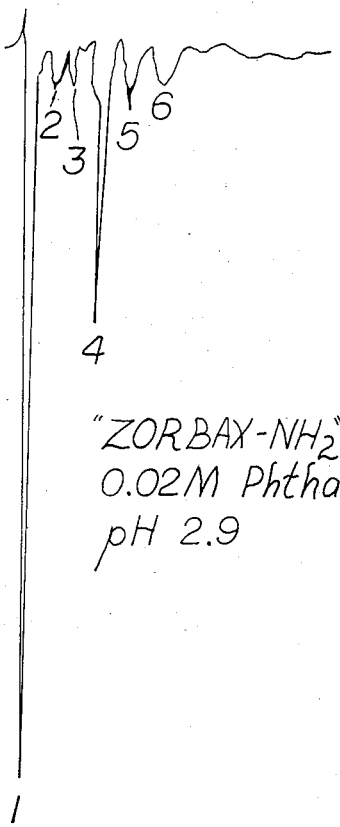
FIGS. 6 and 7 are reproduced chromatograms developed using the method of the invention, and are associated with the teaching of Example 2.

The problem of column overloading as shown in FIG. 6 is not serious, since it can be solved by simply diluting the sample or by using a smaller injection volume.

EXAMPLE 2

Figure 7:
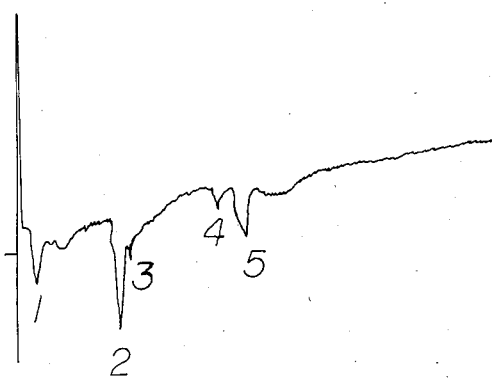

The preceding example was concerned with the sensitivity aspects of the invention. This example illustrates the separation aspects of the invention using a sample containing a plurality of distinct anions. The results of this experiment are shown in FIGS. 6 and 7. The chromatograms of these Figures show excellent resolution of test ions with two commercial brands of weak base ion exchange columns and using two different eluent displacing ion concentrations.

EXAMPLE 3

This example essentially concerns the data compiled and set out in the graph of FIG. 8. This graph is composed of various plots showing k' dependence vs. eluent pH for an eluent composed of 0.02M phthalic acid at 2 ml/min. flow rate, using a duPont Zorbax 4.6 mm I.D.×250 mm long, amino column. The data therein illustrate not only the relationship between k' and eluent pH but also the varying selectivity produced.

What is claimed is:

1. In the method for the chromatographic analysis of transparent sample ions in a solution of photometrically monitorable liquid effluent wherein:

sample is contacted with a flow-through ion exchange medium, and an elution through said ion exchange medium is performed using a liquid eluent which contains photometrically detectable monitor/displacing ions that effectually displace sample ions off the involved ion exchange medium so as to eventually cause displaced sample ions to appear in the effluent from the ion exchange medium;

there is utilized an eluent containing said monitor/displacing ions which are photometrically detectable in said effluent and which are of the same charge but not necessarily the same valence as the sample ions to be detected;

said effluent is photometrically monitored and the concentration of transparent sample ions of interest eluting from the ion exchange medium is indirectly quantitated based on the fluctuation(s) caused by same in the effluent response as produced by the appearance of the transparent sample ions in the effluent causing a concurrent and proportional dip in the concentration of the observed monitor/displacing ions in the effluent;

wherein the improvement comprises:

using a pH dependent variable capacity ion exchange medium that is weakly basic in nature when anions are to be detected and determined from said sample making contact with said medium and using a weakly acidic ion exchange medium when cations are so involved; and using an eluent, the pH of which controls the capacity of the ion exchange medium to a capacity within the range encompassed on the lower end, by the condition which produces overloading and on the upper end, by a capacity which is not greater than about 50 percent of the maximum potential ion exchange capacity of the ion exchange medium whereby the pH of the eluent controls the capacity of the ion exchange medium without detrimentally affecting efficiency of separation.

2. The method of claim 1 wherein the improvement further comprises using as the monitor/displacing ions, ions which absorb radiation in the ultraviolet region, and photometrically monitoring said ions using UV detection.

3. The method of claim 1 wherein the improvement further comprises utilizing a flow-through ion exchange medium which comprises a weakly basic ion exchange medium.

4. The method of claim 3 wherein the improvement further comprises using as the weakly basic ion exchange medium, an amino-containing medium.

5. The method of claim 1 wherein the improvement further comprises utilizing a flow-through ion exchange medium which comprises a weakly acidic ion exchange medium.

6. The method of claim 5 wherein the improvement further comprises using as the weakly acidic ion exchange medium, a medium composed of functional carboxylic ion exchange sites.

7. The method as set forth in any of claims 1, 2, 4 or 6 wherein the improvement further comprises utilizing a balance factor, as defined by the equation:

$$\text{Balance Factor} = \sqrt{(A-B)^2} - \left(\log \frac{1}{C}\right)$$

wherein:
A = the pH of the eluent;
B = the inflection point, in terms of A, of the curve of K′ of an ion of interest in an analysis verses A for a fixed eluent displacing ion concentration used for the analysis and;
C = the molar concentration of the eluent displacing ion used for the analysis, which is maintained between about 1 to about −3.

8. The method of claim 7 wherein the improvement further comprises using an eluent containing monitor/-displacing ions in a molar concentration of up to about $5 \times 10^{-3}$.

9. The method as set forth in any of claims 1, 2, 4 or 6 wherein the improvement further comprises utilizing a balance factor, as defined by the equation:

$$\text{Balance Factor} = \sqrt{(A-B)^2} - \left(\log \frac{1}{C}\right)$$

wherein:
A = the pH of the eluent;
B = the inflection point, in terms of A, of the curve of K′ of an ion of interest in an analysis verses A for a fixed eluent displacing ion concentration used for the analysis and;
C = the molar concentration of the eluent displacing ion used for the analysis, which is maintained between about 0 to about −2.

10. The method of claim 9 wherein the improvement further comprises using an eluent containing monitor/-displacing ions in a molar concentration of up to about $5 \times 10^{-4}$.

11. The method as set forth in any of claims 1, 2, 4 or 6 wherein the improvement further comprises adjusting the capacity of the ion exchange medium between about 0.1 to about 30 percent of the maximum potential ion exchange capacity of the medium.

12. The method of claim 11 wherein the improvement further comprises using an eluent containing monitor/-displacing ions in a molar concentration of up to about $5 \times 10^{-4}$.

13. The method of claim 12 wherein wherein the improvement further comprises utilizing a balance factor, as defined by the equation:

$$\text{Balance Factor} = \sqrt{(A-B)^2} - \left(\log \frac{1}{C}\right)$$

wherein:
A = the pH of the eluent;
B = the inflection point, in terms of A, of the curve of K′ of an ion of interest in an analysis verses A for a fixed eluent displacing ion concentration used for the analysis and;
C = the molar concentration of the eluent displacing ion used for the analysis, which is maintained between about 0 to about −2.

* * * * *

UNITED STATES PATENT AND TRADEMARK OFFICE
CERTIFICATE OF CORRECTION

PATENT NO. : 4,629,705

DATED : Dec. 16, 1986

INVENTOR(S) : Cortes et al.

It is certified that error appears in the above-identified patent and that said Letters Patent is hereby corrected as shown below:

Column 1, line 17, please delete "khym," and insert --Khym,--.

Column 3, line 46, insert -- wherein the improvement comprises: -- before the word "using".

Column 4, line 3, after "( $\log \frac{1}{C}$ )" please insert -- (II) --.

Column 4, line 67, delete "preferbly" and insert -- preferably --.

Column 5, line 15, delete "and" and insert -- an --.

Column 6, line 36, delete "in" and insert -- is --.

Column 9, line 46, delete "flixed" and insert -- fixed --. (Claim 7)

Column 10, line 34, delete "wherein" second occurrence. (Claim 13)

Signed and Sealed this

Ninth Day of February, 1988

*Attest:*

DONALD J. QUIGG

*Attesting Officer*  *Commissioner of Patents and Trademarks*